(12) United States Patent
Habash

(10) Patent No.: US 11,324,737 B1
(45) Date of Patent: May 10, 2022

(54) MODULATING EXPRESSION LEVEL OF A GENE ENCODING A HEAT SHOCK PROTEIN BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 17/330,162

(22) Filed: May 25, 2021

(51) Int. Cl.
| | | |
|---|---|---|
| *A61K 31/45* | (2006.01) | |
| *A61P 9/10* | (2006.01) | |
| *A61P 25/28* | (2006.01) | |
| *A61P 31/00* | (2006.01) | |
| *A61P 35/00* | (2006.01) | |
| *A61P 39/06* | (2006.01) | |

(52) U.S. Cl.
CPC ............... *A61K 31/45* (2013.01); *A61P 9/10* (2018.01); *A61P 25/28* (2018.01); *A61P 31/00* (2018.01); *A61P 35/00* (2018.01); *A61P 39/06* (2018.01)

(58) Field of Classification Search
CPC . A61K 31/45; A61P 9/10; A61P 25/28; A61P 31/00; A61P 39/06; A61P 35/00
See application file for complete search history.

(56) References Cited

PUBLICATIONS

Gariboldi, M. B.,"The nitroxide Tempol modulates anthracycline resistance in breast cancer cells." Free Radical Biology and Medicine 40.8 (2006): 1409-1418.*

Stephanou, et al.,Transcriptional Modulation of Heat Shock Protein Gene Expression, Biochemistry Research International, vol. 2011, Article ID 238601, 8 pages, 2011.

M. Ponomarenko, et al., Heat Shock Proteins, Brenner's Encyclopedia of Genetics (Second Edition), Academic Press, 2013, pp. 402-405.

Li L, et al., Heat Shock Protein 90 Inhibitors: An Update on Achievements, Challenges, and Future Directions. J Med Chem. Mar. 12, 2020;63(5):1798 1822.

Thadeu, et al., Nulgumnalli Manjunathaiah Raghavendra, Carmen Penido, Natural heat shock protein 90 inhibitors in cancer and inflammation, European Journal of Medicinal Chemistry, vol. 189, 2020, 112063, ISSN 0223 5234.

Kim, et al., Heat shock protein 90 is involved in IL 17 mediated skin inflammation following thermal stimulation. International Journal of Molecular Medicine 38.2 (2016): 650 658.

Weeden, et al., HSP90 Inhibition Suppresses Lipopolysaccharide Induced Lung Inflammation In Vivo. PLoS ONE (2015) 10(1): e0114975.

Tuda, et al. HSP90 inhibition modulates NFκB signaling in airway goblet cell metaplasia, bioRxiv preprint doi: https://doi.org/10.1101/2020.05.24.113902.

Tang, et al., Heat shock protein 90alpha (Hsp90α) stabilizes hypoxia inducible factor 1α (HIF 1α) in support of spermatogenesis and tumorigenesis. Cancer Gene Ther (2021).

Minet, et al., Hypoxia induced activation of HIF 1: role of HIF 1α Hsp90 interaction, FEBS Letters, vol. 460, Issue 2, 1999, pp. 251 256.

Bohush, et al., Hsp90 and Its Co Chaperones in Neurodegenerative Diseases. International journal of molecular sciences vol. 20,20 4976. Oct. 9, 2019.

Luo, et al., Heat shock protein 90 in neurodegenerative diseases. Mol Neurodegeneration 5, 24 (2010).

Chatterjee, et al., Targeting Heat Shock Proteins in Cancer: A Promising Therapeutic Approach. International journal of molecular sciences vol. 18,9 1978. Sep. 15, 2017.

Butler, et al., Maximizing the Therapeutic Potential of HSP90 Inhibitors, Mol Cancer Res Nov. 1, 2015 (13) (11) 1445 1451.

Madrigal-Matute, et al., Heat shock protein 90 inhibitors attenuate inflammatory responses in atherosclerosis, Cardiovascular Research, vol. 86, Issue 2, May 1, 2010, pp. 330-337.

Qi, et al., Heat shock protein 90 inhibition by 17 DMAG attenuates abdominal aortic aneurysm formation in mice. American journal of physiology. Heart and circulatory physiology vol. 308,8 (2015).

Song, et al., Antiviral and Anti Inflammatory Activities of Pochonin D, a Heat Shock Protein 90 Inhibitor, against Rhinovirus Infection. Biomolecules & Therapeutics 2018;26:576 583.

Aguilà, et al., Hsp90 as a Potential Therapeutic Target in Retinal Disease. Advances in experimental medicine and biology vol. 854 (2016).

Soule, et al., The chemistry and biology of nitroxide compounds. Free radical biology & medicine vol. 42,11 (2007): 1632 50.

* cited by examiner

*Primary Examiner* — John M Mauro
(74) *Attorney, Agent, or Firm* — Knobbe, Martens, Olson & Bear LLP

(57) ABSTRACT

Some embodiments disclosed herein include a method for decreasing an expression level of a gene. The methods can include identifying a human subject having an increased expression level of HSP90; and administering to the human subject an effective amount of a nitroxide antioxidant, whereby expression level of the gene is decreased.

12 Claims, No Drawings

MODULATING EXPRESSION LEVEL OF A GENE ENCODING A HEAT SHOCK PROTEIN BY TREATING A HUMAN SUBJECT WITH A NITROXIDE

BACKGROUND

Field

The present disclosure relates generally to the field of modulation of gene expression and more particularly to decreasing expression levels of one or more genes relating to heat shock proteins by treating human subjects with a nitroxide.

Description of the Related Art

Diseases and conditions are treatable by adjusting the expression levels and activities of key genes in the body. Gene expression irregularities, whether overexpressed, activated, under expressed or inhibited underlie the development and progression of every disease and condition. Some diseases are characterized by deficient expression of certain genes while other diseases result from over expression of certain genes. A disease resulting from irregular gene expression can be prevented, treated, or reversed by administering a nitroxide antioxidant to target and correct the expression levels of the genes.

Expression levels of genes are often naturally controlled in an appropriate way, but sometimes natural control of gene expression fails. For example, in cancer, genes providing instructions for cell growth are activated or switched on, when they should be off. Autoimmune diseases and aging are other examples of diseases and conditions that result from irregular gene expression. As cells age, the natural control of gene expression deteriorates promoting several diseases and conditions such as inflammation, chronic pain, infections, neurodegenerative disease, neurological disorders, skin diseases, etc. It is essential to identify the irregular expression of the genes involved in the cause of the disease and adjust the expression levels of those genes.

Often referred to as gene therapy, the targeting and correction of cellular dysfunction through adjusting the expression level of certain genes is necessary to prevent, treat, or reverse a disease or condition. Only by identifying key genes and developing therapeutics that altering the expression patterns of those genes can we prevent the development of the disease, reduce its effects once it has occurred, or reverse it all together.

One of the key gene families involved in several diseases and conditions is the heat shock protein encoding gene family. These genes encode heat shock proteins such as heat shock protein 90 (HSP90). When this gene is overexpressed it causes several diseases and conditions associated with the overexpression of the gene. Thus, correction of the overexpression of heat shock protein encoding genes is essential for treatment and prevention of the associated diseases and conditions.

SUMMARY

Some embodiments disclosed herein provide methods for decreasing gene expression. The methods, in some embodiments, include identifying a human subject over the age of 35 and having an increased expression level of HSP90; and administering to the human subject an effective amount of a nitroxide antioxidant resulting in a decreased expression level of the gene. In some embodiments, the gene is HSP90. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: identifying a human subject having an increased expression level of HSP90; administering to the human subject an effective amount of a nitroxide antioxidant, whereby the expression level of HSP90 is decreased. In some embodiments, the gene is HSP90. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to an increased expression level of HSP90; administering to the human subject an effective amount of a nitroxide antioxidant, whereby the expression level of HSP90 is decreased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is HSP90. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of a decreased expression level of a HSP90 gene; administering to the human subject an effective amount of a nitroxide antioxidant, whereby the expression level of the gene associated with heat shock proteins and heat shock protein activity is decreased. In some embodiments, the cancer can be selected from the group consisting of bladder cancer, colorectal cancer, hepatocellular carcinoma, prostate carcinoma, and kidney carcinoma. In some embodiments, the gene is HSP90. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of a decreased expression level of a HSP90 gene; administering to the human subject an effective amount of a nitroxide antioxidant, wherein the expression level of the gene associated with heat shock proteins and heat shock protein activity is decreased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is HSP90. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased expression level of heat shock proteins and heat shock protein activity is decreased in a patient in need thereof, comprising: identifying a human subject having or at risk of developing a disease associated with an increased expression of HSP90; administering to the human subject an effective amount of a nitroxide antioxidant, whereby the expression level of HSP90 is decreased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is HSP90. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of a decreased expression level of HSP90; and administering to the individual an effective amount of a nitroxide antioxidant to increase the level of expression of the gene associated with heat shock proteins and heat shock protein activity. In some embodiments, the gene is HSP90. In some embodiments, the human subject is over the age of 45. In some embodiments, the human subject is over the age of 55. In some embodiments, the human subject is over the age of 65. In some embodiments, the human subject has an increased expression level of the gene. In some embodiments, the individual has or is at risk of developing an age-related condition. In some embodiments, the age-related condition comprises decreased senescence in a tissue. In some embodiments, the age-related condition comprises inhibition heat shock proteins and heat shock protein activity in a tissue. In some embodiments, the age-related condition comprises decreased molecular heterogeneity. In some embodiments, the age-related condition comprises decreased functional impairment in a tissue. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related increased expression level of HSP90; and administering to the individual an effective amount of a nitroxide antioxidant to increase the level of expression of the gene associated with heat shock proteins and heat shock protein activity. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is HSP90. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with heat shock proteins and heat shock protein activity is decreased. In some embodiments, the individual has an increased expression level of the gene. In some embodiments, the gene is HSP90. In some embodiments, the condition is an age-related condition. In some embodiments, the age-related condition comprises increased senescence in a tissue. In some embodiments, the age-related condition comprises hyperactivation of HSP90 in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Some embodiments disclosed herein provide methods for increasing the expression level of a gene in a human subject in need thereof, comprising: identifying a human subject having an increased expression level of HSP90; and delivering to the human subject an effective amount of a nitroxide antioxidant to increase the level of expression of the gene associated with heat shock proteins and heat shock protein activity. In some embodiments, the nitroxide antioxidant is 4-hydroxy-2,2,6,6-tetramethylpiperidine-1-oxyl. In some embodiments, the increased expression level of the gene is age-related. In some embodiments, wherein the increased expression level of the gene is cancer-related. In some embodiments, the increased expression level of the gene is disease-related. In some embodiments, the increased expression level of the gene is neurodegeneration-related. In some embodiments, the increased expression level of the gene is infection related. In some embodiments, the increased the level of expression of the gene improves heat shock protein activity and mitochondrial function. In some embodiments, the expression level of the gene is increased in a tissue selected from the group consisting of a skin tissue, an immune tissue, an adipose tissue, a pancreatic tissue, cardiac tissue, and a neuronal tissue by treatment.

Some embodiments disclosed herein provide methods for increasing an expression level, in an eukaryotic cell, of one or more genes encoding heat shock proteins involved in mitochondrial heat shock by contacting the eukaryotic cell with a nitroxide antioxidant. In some embodiments, the one or more genes is HSP90. In some embodiments, the nitroxide antioxidant is 4-hydroxy-2,2,6,6-tetramethylpiperidine-1-oxyl. In some embodiments, the eukaryotic cell is a cancer cell. In some embodiments, the expression level of the one or more genes is increased in said cell in a tissue selected from the group consisting of a skin tissue, an immune tissue, an adipose tissue, a pancreatic tissue, cardiac tissue, and a neuronal tissue. In some embodiments, prior to said contacting, the eukaryotic cell exhibits an age-related increased expression level of said one or more genes. In some embodiments, prior to said contacting, the eukaryotic cell exhibits a disease-related increased expression level of said one or more genes. In some embodiments, prior to said contacting, the eukaryotic cell exhibits a neurodegeneration-related expression level of said one or more genes.

Some embodiments disclosed herein provide methods for improving chemotherapeutic response in a human subject comprising: contacting cancer cells in the subject with an effective amount of a nitroxide antioxidant whereby a level of expression of heat shock proteins and heat shock protein activity is decreased in said cancer cells. In some embodiments, said cancer cells are known to have increased HSP90 function. In some embodiments, the decreased expression level of one or more genes following treatment initiates apoptosis within one or more of said cancer cells. In some embodiments, the decreased expression level reduces or prevents resistance to other chemotherapeutic agents. In some embodiments, the nitroxide antioxidant is 4-hydroxy-2,2,6,6-tetramethylpiperidine-1-oxyl. In some embodiments, the gene is selected from the group consisting of HSP90.

Some embodiments disclosed herein provide methods for increasing heat shock proteins and heat shock protein activity in a human subject comprising: identifying a human subject known to have increased HSP90 activity; and delivering to the subject an effective amount of a nitroxide antioxidant, whereby a level of heat shock proteins and heat shock protein activity is decreased. In some embodiments, the nitroxide antioxidant is 4-hydroxy-2,2,6,6-tetramethylpiperidine-1-oxyl. In some embodiments, increased HSP90 function is age-related. In some embodiments, the increased HSP90 function is cancer-related. In some embodiments, the increased HSP90 function is disease-related. In some embodiments, the increased HSP90 function is neurodegeneration-related. In some embodiments, the increased HSP90 function is infection-related. In some embodiments, the increased level of expression of the gene improves remodeling of damaged tissues. In some embodiments, the expression level of the gene is increased in a tissue selected from the group consisting of a skin tissue, an immune tissue, an adipose tissue, a pancreatic tissue, cardiac tissue, and a neuronal tissue following treatment.

Some embodiments disclosed herein provide methods for treating a human subject having cancer comprising: delivering an effective amount of a nitroxide antioxidant to a human subject, wherein the human subject has previously been administered at least one chemotherapeutic agent, whereby a level of expression of heat shock proteins and heat shock protein activity is decreased. In some embodiments, the human subject having cancer is identified with an increased expression of HSP90. In some embodiments, the methods further comprise administering a promotor of a HSP90 to the human subject.

DETAILED DESCRIPTION

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology $2^{nd}$ ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g., an unspliced RNA, an mRNA, a splice variant mRNA, a polypeptide, a posttranslationally modified polypeptide, a splice variant polypeptide etc., and specifically products made using an RNA gene product as a template, e.g., cDNA of the RNA.

As used herein, "differential expression" of a gene means that the expression of the gene is at a higher level ("decreased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to decrease by treating the human subject with a compound, for example a nitroxide antioxidant, such that the expression level of the gene after treatment is lower than the expression level of the gene before treatment in the human subject.

As used herein, "delivering" a compound shall mean bringing that compound into contact with a relevant cell, tissue, or organism. Similarly, "contacting" shall mean that the compound contacts a relevant target, such as a tissue or cell or tumor. In either case, delivery or contact in an organism is affected by directly administering the compound to the organism, or by administering a different compound to the organism, such as a prodrug that is converted in vivo to the desired compound. In short, these terms cover any action that leads to contact between the desired compound and a target cell, tissue, or organism.

The present disclosure describes methods of modulating gene expression in human subjects. However, this is illustrative only and not intended to be limiting. For example, the methods disclosed herein can be used for modulating gene expression in other vertebrates, such as but not limited to mammals, birds, reptiles, fish, and the like (with modifications wherein appropriate). Mammals and birds include most agricultural animals. Treatment of companion animals, e.g., dogs, cats, or birds is also contemplated.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating alteration in gene expression, such as age-related, cancer-related, disease-related, neurodegeneration-related, and infection-related alteration in gene expression. Gene expression changes also play important roles in aging and serve as biomarkers of physiological decline and disease conditions, such as neurodegenerative diseases, and cancers. Therefore, one aspect of the present disclosure is methods of treating a human subject having an age-related, cancer-related, disease-related, neurodegeneration related, and/or infection-related decrease in gene expression levels, such as those genes associated with heat shock proteins and heat shock protein activity. In some embodiments, the human subject can be identified based on the human subject's age, gene expression level, family history, health conditions, medical history, habits, or a combination thereof.

Regardless of the cause of the upregulation, some common terminology can be used. In some embodiments, the expression level of a gene (e.g., HSP90) in a human subject is considered to be upregulated or increased if the increase in the expression level of that gene is statistically significant compared to that of a control or a reference. In some embodiments, the expression level of a gene (e.g., HSP90) in a human subject is considered to be upregulated or increased if the increase in the expression level of that gene is statistically significant compared to that of a control or a reference.

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The increase in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the increase in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, or is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of HSP90. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™) Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Targeted Gene Expression Adjustment

All living organisms are comprised of cells that function individually as well as in combination with other cells to form larger and more complex structures such as tissue and organs. The operation of each cell is based on the genetic instructions provided by the DNA contained therein. DNA is arranged in a particular sequence referred to as a gene which is transcribed and translated into a functional product required for the operation of the cell.

Genes are expressed in a particular quantity based on the instruction provided by the DNA. In particular, gene expression describes transcription of gene encoding DNA sequences into complementary DNA (cDNA) and translation of cDNA into the functional products, such as proteins. Many factors, both internal and external, are involved in regulation of gene expression in cells. Such regulation manifests in an adjustment of gene expression to increase or decrease a number of proteins made.

The quantity of expression for a particular gene or group of complementary genes can be considered relative to a healthy state or disease state of the cell. In a healthy state, genes are expressed in a predictable quantity necessary for the operation of the cell. In a disease state, the genes are overexpressed or under expressed relative to the healthy-state expression. The deviation from the healthy state of gene expression results in catastrophic burden on the cell due to over or under production of the functional product encoded by the gene.

A condition or disease is identifiable based on such dysfunctional expression of genes within the cell. Whether the dysfunctional expression of the genes is due external influence on the cell or genetic aberrations, correction to the dysfunctional expression is necessary to address the underlying cause of the condition or disease. Overexpression or under expression of a gene or genes often results in dysfunction of downstream actions controlled by the same. Whether the gene is a regulator of cellular function or a vital in a responsive mechanism, modulation of the gene expression is a fundamental directive in addressing the foundational issues associated with many diseases and conditions. Differences often exist in therapy directives. Treatments for a disease or condition are often directed at addressing a manifestation or symptom of the disease. However, the underlying disease is permitted to remain resulting in subsequent presentation of the previously treated symptoms. Therefore, it is essential to correct or reinforce the underlying cause of the disease. Ultimately, the treatment of the disease or condition requires targeting and modulating the expression level of the gene or genes that are inappropriately overexpressed or under expressed.

In a healthy state, the heat shock proteins regulate the formation, organization, and clearance of dysfunctions proteins within the cell. When the genes that encode these proteins are overexpressed, their corresponding function is increased or hyperactive, which results in the development and progression of disease. Whether the inducement of these proteins is reactive, or due to a genetic abnormality, it is the dysfunctional expression that defines a disease state for the subject.

Certain conditions, such as vascular diseases, neurodegenerative disease, cancer, diabetes, obesity, and aging are associated with (e.g., causes or caused by) overexpression of heat shock protein encoding genes resulting in the elevated activity and disfunction of vital cellular processes within cells and tissues. Thus, modulation of overexpressed or elevated heat shock protein genes is essential for treatment and prevention of diseases and conditions.

Genes Associated with Heat Shock Proteins and Heat Shock Protein Activity

In some embodiments, administering to the human subject an effective amount of the nitroxide antioxidant results in a decreased expression level of a gene, for example HSP90. Therefore, some embodiments disclosed herein provide methods for treating an individual in need thereof, comprising identifying an individual having a disease-related increased expression level of HSP90; and administering to the individual an effective amount of a nitroxide antioxidant to decrease the level of expression of HSP90. Some embodiments disclosed herein provide methods for treating an individual in need thereof, comprising identifying an individual in need of a decreased expression level of a HSP90 gene; and administering to the individual an effective amount of a nitroxide antioxidant to decrease the level of expression of HSP90. Some embodiments disclosed herein provide methods for treating an individual in need thereof, comprising: administering to the individual, known to have a disease-related increased expression level of HSP90, an effective amount of a nitroxide antioxidant to increase the level of expression of HSP90. Some embodiments disclosed herein provide methods for treating an individual in need thereof, comprising: administering to an individual, known to be in need of a decreased expression level of a HSP90 gene, an effective amount of a nitroxide antioxidant to increase the level of expression of heat shock proteins and heat shock protein activity.

Non-limiting examples of diseases associated with altered level of heat shock proteins and heat shock protein activity include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infections, infectious diseases; bacterial infections; inflammatory responses; viral infections; autoimmune diseases; systemic lupus erythematosus; autoimmune lymphoproliferative syndrome; rheumatoid arthritis; and thyroiditis.

The gene associated with heat shock proteins can be Ubiquitin, HSP10, HSP27, Ab-crystallin, HSP40, HSP47 HSP60, HSP70, HSP72, HSP73, HSP75, HSP90, HSP110, HSP110, HSP105. Additionally, HSP90 is associated with and has been previously referred to as HSP90AA1, HSPC1, HSPCA, HSP89, FLJ31884, HSP90N, HSP90AA3P, HSP-CAL1, HSP90AB1, HSPC2, HSPCB, HSP90B1, TRA1, GP96, GRP94, TRAP1, HSP75, HSP90L. For example, the treatment results in decreased expression levels of HSP90. The a decreased expression level of HSP90, decreases heat shock protein quantity and heat shock protein activity. The decreased level of HSP90 results in a decrease in or disappearance of signs and symptoms of a disease associated with increased HSP90 function, including the curing of the disease associated with increased HSP90 function. In some embodiments, the decreased expression level of HSP90, decreases the level of heat shock proteins and heat shock protein activity. The decreased level of heat shock proteins and heat shock protein activity results in a decrease in or disappearance of signs and symptoms of the disease associated with increased HSP90 function, including the curing of the disease associated with increased HSP90 function. In some embodiments, the decreased level of heat shock proteins and heat shock protein activity inhibits, suppress, prevents, or reverses the disease or the symptoms associated with the disease.

Heat Shock Proteins

Heat shock proteins (HSPs) are absolutely necessary for life. They are considered "chaperone" proteins because they chaperone and organize RNA sequences into protein structures. Proteins are the functional unit of the cell that are formed based on instruction provided by one or more genes. Proteins result from a long chain of amino acid sequences and these amino acids each have unique properties. For example, some amino acids are hydrophobic, others are lipophobic which causes them to organize in a complex manner forming a protein. The heat shock proteins are necessary to regulate the organization and formation of the proteins.

The induction of Hsps in response to various stresses is dependent on the activation of specific members of a family of transcription factors, the heat-shock factors (HSFs) which bind to the heat-shock element (HSE) in the promoters of the genes encoding Hsps. Four HSFs (HSF1 to 4) have been cloned from a number of organisms and their roles have now been characterized. For example, HSF1 and HSF3 have been shown to be involved in regulating Hsps in response to thermal stress whereas HSF2 and HSF4 are involved in Hsp regulation in unstressed cells and their levels are regulated in response to a wide variety of biological processes such as immune activation and cellular differentiation. In general, however, the stimuli which induce such alterations in Hsp gene expression under nonstress conditions are poorly characterized and the mechanisms by which they act are unclear. In this paper, we discuss recent studies indicating that Hsps are not only regulated by HSFs alone, but also by transcription factors which are able to interact or cooperate with HSF1 and modulate the transcriptional regulation of Hsps in response to nonstressful stimuli. More recently, as will be explained later, it has also been reported that HSF2, like HSF1 also play a role as a stress-inducible factor in promoting the induction of Hsps under certain conditions. (Anastasis Stephanou, David S. Latchman, "Transcriptional Modulation of Heat-Shock Protein Gene Expression", Biochemistry Research International, vol. 2011, Article ID 238601, 8 pages, 2011. https://doi.org/10.1155/2011/238601).

In certain instances, HSPs may be induced by transcriptional factors such as STAT1, STAT3, and NF-IL6. When evaluating different disease states, several studies have found that incidence, progression, and poor prognosis correlate with elevated levels of HSP90. In several disease states, such as SLE, diabetes and cancer, there was also a correlated increase in the pro-inflammatory cytokine IL-6. (Stephanou, 2011).

Heat shock proteins are specific proteins that are made when cells are briefly exposed to temperatures above their normal growth temperature. The synthesis of HSPs is a universal phenomenon, occurring in all plant and animal species studied, including humans. HSPs are also made by prokaryotic cells, namely, bacterial and archaean. Because HSPs can also be induced by oxidants, toxins, heavy metals, free radicals, viruses, and other stressors, they are sometimes called the 'stress proteins'. Most HSPs are molecular chaperones, which normally promote the self-assembly of newly synthesized polypeptide chains of proteins into a native spatial structure, the assembly of their complexes, and their transport through membranes as well as their participation in signal transduction. A nonlethal increase in temperature above the physiological norm for a biological species suppresses protein synthesis in the cell, activates the heat shock factor (HSF), and enhances transcription of heat shock genes, while exposure to a lethal temperature initiates apoptosis or programmed cell death. In turn, HSPs inhibit apoptosis and provide cells with thermal stability if stress reoccurs. (M. Ponomarenko, I. Stepanenko, N. Kolchanov, Heat Shock Proteins, Brenner's Encyclopedia of Genetics (Second Edition), Academic Press, 2013, Pages 402-405, ISBN 9780080961569, https://doi.org/10.1016/B978-0-12-374984-0.00685-9.)

Hsp90 is one of the most important chaperones involved in regulating the maturation of more than 300 client proteins, many of which are closely associated with refractory diseases, including cancer, neurodegenerative diseases, and viral infections. (Li L, Wang L, You Q D, Xu XL. Heat Shock Protein 90 Inhibitors: An Update on Achievements, Challenges, and Future Directions. J Med Chem. 2020 Mar. 12; 63(5):1798-1822. doi: 10.1021/acs.jmedchem.9b00940. Epub 2019 Nov. 12. PMID: 31663736.) Furthermore, HSP90 is the most abundant HSPs, which are chaperone molecules whose major roles are cell protection and maintenance by means of aiding the folding, the stabilization and the remodeling of a wide range of proteins. A few hundreds of proteins depend on HSP90 chaperone activity, including kinases and transcriptional factors that play essential roles in cancer and inflammation, so that HSP90-targeted therapies have been considered as a potential strategy for the treatment of cancer and inflammatory-associated diseases. HSP90 inhibition by natural, semi-synthetic and synthetic compounds have yield promising results in pre-clinical studies and clinical trials for different types of cancers and inflammation. (Thadeu E. M. M. Costa, Nulgumnalli Manjunathaiah Raghavendra, Carmen Penido, Natural heat shock protein 90 inhibitors in cancer and inflammation, European Journal of Medicinal Chemistry, Volume 189, 2020, 112063, ISSN 0223-5234, https://doi.org/10.1016/j.ejmech.2020.112063).

The function of members of the heat shock protein family is diverse and crucial for cellular function and development. Overexpression and elevated activity or function of the heat shock proteins is directly and indirectly responsible for the development of diseases and conditions relating to the dysfunctional operation of the encoded proteins.

HSP90

HSP90 is a chaperone protein that assists other proteins to fold properly, stabilizes proteins against heat stress, and aids in protein degradation. It also stabilizes a number of proteins relating to hypoxic conditions such as cancer and tumorgenesis. It is one of the most common of the heat-related proteins. The "90" comes from the fact that it weighs roughly 90 kiloDaltons. A 90 kDa protein is considered fairly large for a non-fibrous protein. First discovered in cells subjected to significant amounts of stress such as heat and hypoxia, it was initially associated with inducement under stressful conditions. Later, it was discovered that HSP90 played a significant role in both stressful and healthy-state conditions.

In unstressed cells, HSP90 plays a number of important roles, which include assisting folding, intracellular transport, maintenance, and degradation of proteins as well as facilitating cell signaling.

Inflammatory Skin Diseases

The cause and progression of inflammatory skin diseases often involves interactions between immune cells and keratinocytes. Keratinocytes perform important functions in the regulation of inflammation and respond to environmental and pro-inflammatory stimuli, including the cytokines interleukin (IL)-17 and IL-22 which are produced by T helper 17 (Th17) cells. Following stimulation with IL-17, Act1 is recruited to the IL-17 receptor, followed by the activation of the kinase transforming growth factor β-activated kinase 1 (TAK1) and the IκB kinase (IKK) complex, which subsequently activates nuclear factor-κB (NF-κB). It has been shown that IL-17 enhanced skin inflammation by stimulating the secretion of IL-1β by keratinocytes through the NLR family, pyrin domain containing 3 (NLRP3)-caspase-1 pathway. Act1 is a client protein of HSP90 and HSP90 activity is required for IL-17 signaling. (Kim, B., Park, M., Kim, J., Lee, K., Woo, S."Heat shock protein 90 is involved in IL-17-mediated skin inflammation following thermal stimulation". International Journal of Molecular Medicine 38.2 (2016): 650-658.).

In inflammatory skin diseases such as psoriasis, HSP90 functions as a chaperone that facilitates the folding and assembly of its client proteins. Loss of HSP90 chaperone function results in the degradation of its client proteins. HSP90 is constitutively expressed in human keratinocytes and fibroblasts in vitro and is focally expressed in epidermal layers in vivo. The epidermal expression of HSP90 is upregulated by external stimuli, such as heat and chemical stress. In addition, increased HSP90 expression in keratinocytes and mast cells from the skin of patients with psoriasis has been reported. Psoriasis is a chronic inflammatory skin disease characterized by keratinocyte hyperplasia, dermal leukocyte infiltration and vascular enhancement. The cytokine milieu, through activation of Th1 and Th17 cells, contributes to the establishment of skin inflammation. (Kim, 2016). Inhibition of HSP90 in patients with an inflammatory skin disease can reduce the signs and symptoms of the disease. Administration of a nitroxide antioxidant to reduce the expression level and activity of HSP90 can prevent the formation of such diseases by priming cells prior to exposure to the external stimuli to promote improved resistance to the development of the disease by reduced interaction with IL17.

Inflammation and Related Diseases Associated with Increased HSP90

Several studies have shown that elevated expression and activity of HSP90 is associated with increased inflammation and associated inflammation-mediated diseases. (Lilja A, Weeden C E, McArthur K, Nguyen T, Donald A, Wong Z X, et al. (2015) HSP90 Inhibition Suppresses Lipopolysaccharide-Induced Lung Inflammation In Vivo. PLoS ONE 10(1): e0114975. https://doi.org/10.1371/journal.pone.0114975). In particular, it has been shown that increased HSP90 expression and activity are associated with inflammatory conditions, in particular, those involving the respiratory system such as asthma and chronic obstructive pulmonary disease. HSP90 is often secreted from within a cell and functions extracellularly. Such extracellular protein can be pathogenic as HSP90 is elevated in the blood of patients with chronic obstructive pulmonary disease (COPD). (Id.).

Additionally, chronic muco-obstructive lung diseases such as asthma, chronic bronchitis, and cystic fibrosis are a major cause of mortality and disability worldwide. There are currently no curative treatments for most patients with chronic muco-obstructive diseases. Various environmental triggers can activate pathways that cause airway goblet cell metaplasia. One pathway that has been well characterized is the T helper 2 (Th2) pathway in which interleukin 13 (IL-13) activates downstream signaling that ultimately results in goblet cell metaplasia. Th2 signaling drives disease in approximately half of people with asthma. Th17 signaling drives goblet cell metaplasia in some people with asthma, chronic bronchitis, and cystic fibrosis. In many patients with chronic airway goblet cell metaplasia, the driving mechanism is unknown.

HSP90 is important for both IL-13- and IL-17-induced goblet cell metaplasia. HSP90 inhibition blocks and reverts IL-13- and IL-17-induced goblet cell metaplasia in human airway epithelia cells in vitro and in mice in vivo. HSP90 is a chaperone protein required in the proper folding and stabilization of hundreds of client proteins. HSP90 inhibitors act on the ATPase activity of HSP90 and results in ubiquitination and proteasomal degradation of its clients. Various HSP90 clients are important in goblet cell metaplasia, including Akt, Jak/STAT, IRS, Notch, and kinases important for NFκB signaling. (HSP90 inhibition modulates NFκB signaling in airway goblet cell metaplasia, Rosarie A. Tudas, Ryan M. Gannon, Andrew L. Thurman, Mallory R. Stroik, Joseph Zabner, Alejandro A. Pezzulo, bioRxiv 2020.05.24.113902; doi: https://doi.org/10.1101/2020.05.24.113902).

Accordingly, treatment with a nitroxide antioxidant such as Tempol decreases HSP90 to confer a beneficial and positive impact in a subject having respiratory inflammation. More specifically, the reduction in expression level of HSP90 treats several different diseases caused by respiratory inflammation associated with an increased expression of HSP90.

Hypoxia and Destabilization of HIF1a

Hypoxia-inducible factor-1 (HIF-1a), a master transcriptional factor for protecting cells from hypoxia, plays a critical role in spermatogenesis and tumorigenesis. Increase in HSP90 is known to stabilize HIF1a in hypoxic conditions. For this and a direct impact on the regulation of protein synthesis, reducing expression levels of HSP90 also reduces the activity of HIF1a resulting in apoptosis in cancer cells. Several cancers have been researched including breast, GIST, leukemias, pancreatic, lung (small cell and non-small cell), etc. In particular, In HIF-1α-dependent tumor cells, we found that Hsp90α forms protein complexes with hypoxia-elevated HIF-1α and Hsp90α knockout prevents hypoxia-induced HIF-1α accumulation. (Tang, X., Chang, C., Hao, M. et al. Heat shock protein-90 alpha (Hsp90α) stabilizes hypoxia-inducible factor-1α (HIF-1α) in support of spermatogenesis and tumorigenesis. Cancer Gene Ther (2021). https://doi.org/10.1038/s41417-021-00316-6).

Hsp90 molecular chaperone as a novel VHL- and oxygen-independent regulator of HIF-1α protein stability. Inhibition of HSP90 has been shown to destabilize both pre-existing and newly synthesized HIF-1α protein pools became unstable, although the rate of HIF-1α synthesis remained essentially unchanged. (Isaacs, 2002). E Minet, D Mottet, G Michel, I Roland, M Raes, J Remade, C Michiels, Hypoxia-induced activation of HIF-1: role of HIF-1α-Hsp90 interaction, FEBS Letters, Volume 460, Issue 2, 1999, Pages 251-256, ISSN 0014-5793, https://doi.org/10.1016/S0014-5793(99)01359-9.).

Administration of a nitroxide antioxidant promotes destabilization of HIF1a through downregulation and inhibition of HSP90. The destabilization of HIF1a is vital to treat several different diseases caused by hypoxia or hyperactivity of HIF1a. For example, cancer and tumorigenesis rely on HIF1a to promote survival of cancer cells in rapidly growing conditions. Decreasing HSP90 destabilizes HIF1a in these cells promoting apoptosis and reducing the rate of tumor growth as well as treating the underlying cancer.

Neurodegerative Diseases

Folding into a defined three-dimensional structure is crucial for proteins to achieve functional activity in the cell. Proteins often fail to preserve their structure when cells are exposed to stress, such as high temperature, toxic chemicals, and others. These factors often lead to protein misfolding and formation of protein aggregates. Accumulation of these aggregates is a burden for the cell, since it leads to major dysregulation of cellular metabolism. Protein aggregates can be found in at least 30 different human diseases, including various neurodegenerative diseases. (Bohush, Anastasiia et al. "Hsp90 and Its Co-Chaperones in Neurodegenerative Diseases." International journal of molecular sciences vol. 20, 20 4976. 9 Oct. 2019, doi:10.3390/ijms20204976). In particular, Alzheimer's Disease (AD) where HSP90 overexpression is associated with increased Tao protein and plaque formation due to dysfunctional protein aggregation. Molecular chaperones and their co-chaperones are proteins that assist other proteins in proper folding into three-dimensional structures to attain functionality. The key role of molecular chaperones is to prevent protein aggregation, especially under conditions of cellular stress. Expression of chaperones is often induced by heat shock, oxidative stress, toxic chemicals, or inflammation. During aging for example, the imbalance between chaperone/co-chaperone levels and activity in neurons seems to be responsible for a decline in protein folding. Thus, in general, one may assume that this imbalance contributes to the development of age-related neurodegenerative diseases.

AD is a progressive neurodegenerative disorder characterized by cognitive impairment accompanied by language, visuospatial, and motor dysfunctions. The histopathological hallmark of AD is the extracellular accumulation of amyloid-β (Aβ) in senile plaques and formation of intracellular neurofibrillary tangles (NFTs). Amyloid plaques consist of β-amyloid (Aβ) peptides, which are derived as a result of cleavage of the amyloid precursor protein (APP). The mechanism of HSP90 in AD involves phosphorylation of tau that is regulated by a Hsp90 co-chaperone, Cdc37, which co-localizes and interacts with tau in the human brain. It was shown that knock-down of Cdc37 in HeLa cells might influence the stability of tau kinases, such as Cdk5 and Akt. Additionally, suppression of Cdc37 destabilizes tau and leads to its clearance, whereas Cdc37 overexpression maintains tau level in these cells. The level of Cdc37 significantly increases with age and contributes to the tau phosphorylation profile, altering toxicity and stability of this protein. (Bohush, 2019).

Another mechanism of action relating to HSP90 overexpression in the development of neurodegenerative diseases involves HSP90 maintaining the functional stability of neuronal proteins of aberrant capacity, thus, allowing and sustaining the accumulation of toxic aggregates. (Luo, W., Sun, W., Taldone, T. et al. Heat shock protein 90 in neurodegenerative diseases. Mol Neurodegeneration 5, 24 (2010). https://doi.org/10.1186/1750-1326-5-24). Inhibition of HSP90 provides a significant opportunity for beneficial treatment of several different neurodegenerative disorders associated with elevated HSP90 and increased toxic aggregation. Administration of Tempol to inhibit HSP90 serves as a therapeutic offering significant benefit in treatment and therapy regiments for these diseases.

Cancer

HSPs are overexpressed in a wide range of tumor types. Elevated levels of HSP expression in specific cancers usually portend a poor prognosis and increased resistance to therapies [13]. Elevated expression of HSPs in transformed cells plays a vital role in suppression of apoptosis, spontaneous as well as triggered by therapeutic interventions, which is an important characteristic role of HSPs aiding tumor progression and resistance to treatment. In the cancer cell, the increased levels of HSP is reinforced by a hyperactivation of HSF1, which itself helps promote invasion and metastasis. (Chatterjee, Suman, and Timothy F Burns. "Targeting Heat Shock Proteins in Cancer: A Promising Therapeutic Approach." International journal of molecular sciences vol. 18, 9 1978. 15 Sep. 2017, doi:10.3390/ijms18091978). HSP90 relies on its ability to bind and hydrolyze ATP in order to effectively regulate the maturation of its so-called "client" proteins through a conformationally dynamic ATPase-driven cycle, controlled by an orchestrated set of interactions with a range of co-chaperones. (Maximizing the Therapeutic Potential of HSP90 Inhibitors, Lisa M. Butler, Roberta Ferraldeschi, Heather K. Armstrong, Margaret M. Centenera and Paul Workman, Mol Cancer Res Nov. 1 2015 (13) (11) 1445-1451; DOI: 10.1158/1541-7786.MCR-15-0234).

HSP90 plays a critical role in malignant transformation HSP90 is evolutionary conserved and ubiquitously expressed playing crucial roles in the folding, stabilization, activation, maturation, function and proteolytic degradation of several client proteins that are bona fide oncoproteins involved in multiple tumor types. The clientele includes many oncogenic kinases including ERBB2, EGFR, CDK4, BRAF, CRAF, HER2, AKT, MET, MEK, and BCR-ABL (breakpoint cluster region-Abelson), as well as critical transcription factors such as estrogen and androgen receptors, p53 and HIF-1α. The catalytic subunit of telomerase hTERT and survivin are some other examples of cancer-related clients of HSP90. Association of Hsp90 with its clients is regulated via its N-terminal ATPase domain, and its activity is further modulated by binding of co-chaperones, which promotes the formation of client specific super-chaperone complexes. Suppression of HSP90 expression can lead to simultaneously co-inhibition of wide range of client proteins thereby affecting multiple signaling pathways, thereby antagonizing all of the hallmark pathological characteristics of cancerous cells including self-sufficiency in growth signals, non-responsiveness to signals that suppresses growth, apoptosis evasion, gaining uncontrolled replicative potential, angiogenesis, invasiveness and metastasis. (Chatterjee, 2017). Since abnormal levels of Hsp90 have been observed in malignant cells and inflamed tissues, this chaperone is particularly in the focus of scientific interest in the context of the treatment of cancer and autoimmune/inflammatory diseases (Shukla and Pitha 2012; Li et al. 2013; Tukaj et al. 2013). Hsp90 participates in stabilizing and activating more than 200 'client' proteins, including key signaling molecules, such as nuclear transcription factors (e.g., NF-κB, STATs, and p53) and kinases (e.g., Raf/MEK/ERK, PI3K/AKT, and p38/MAPK). Thus, it regulates crucial cellular processes, e.g., inflammation, growth, survival, differentiation, and apoptosis (Trepel et al. 2010). Many oncoproteins may also belong to the 'clients', therefore a therapy based on Hsp90 inhibition is currently carried out in several clinical trials (phase I-III) as a promising strategy for the treatment of patients with different types of cancer (Garcia-Carbonero et al. 2013).

Vascular Diseases

HSP90 has been identified as a cause of several different types of vascular diseases. The function and role of HSP90 in causing and promoting vascular diseases involves different biological pathways and processes. For example, studies have shown that inhibition of HSP90 modulates HSP70 levels and inflammatory signaling pathways in vascular cells. (Julio Madrigal-Matute, Oscar Lopez-Franco, Luis Miguel Blanco-Colio, Begoña Munoz-Garcia, Priscila Ramos-Mozo, Luis Ortega, Jesus Egido, Jose Luis Martin-Ventura, Heat shock protein 90 inhibitors attenuate inflammatory responses in atherosclerosis, Cardiovascular Research, Volume 86, Issue 2, 1 May 2010, Pages 330-337, https://doi.org/10.1093/cvr/cvq046).

Atherothrombosis is the leading cause of mortality in the Western world. The underlying pathological process is a thickening of the arterial wall. However, it has been increasingly realized that lesions responsible for acute events may not necessarily be critically obstructive. Attenuation of the fibrous cap is a main determinant of plaque stability since the cap confers resistance to rupture due to its composition of collagen and other extracellular matrix (ECM) proteins, synthesized by vascular cells. Inflammatory cells are able to release different proteases, which lead to degradation of ECM proteins and promote plaque instability and rupture. It has been established that the breakdown of atherosclerotic plaques occurs more frequently in thin cap atherosclerotic plaques and where there is a great amount of inflammatory cells. Here, we see that HSP90 levels were higher in those plaques where the fibrous cap was thinner, suggesting that HSP90 plays an important role in the instability of advanced human atherosclerotic plaques. (Madrigal-Matute, 2010).

The elevated HSP90 level associated with these atherosclerotic plaques promotes disease progression. Particularly, considering the different client proteins of HSP90 involved in inflammatory diseases, STAT and NF-κB are the most relevant. It is understood that JAK/STAT is an important signaling pathway that functions downstream cytokine receptors and regulates the initiation/progression of atherosclerosis and the remodeling in response to injury. The inhibition of HSP90 is essential to properly regulate these pro-inflammatory pathways in order to prevent and reduce the development of atherosclerosis. (Id.).

In neurovasculature, studies have shown that mice overexpressing HSP70 showed decreased number of activated macrophages and inhibition of NF-κB in a model of brain inflammation. (Id.). As discussed above, HSP90's role of regulating HSP70 is crucial in this regard to prevent vascular instability and disease development in the brain. Such treatment and modulation of HSP90 in neuronal tissue is effectively accomplished by a nitroxide antioxidant such as Tempol, which is known to cross the blood brain barrier.

Another example of an embodiment of the present invention as it relates to the treatment of vascular diseases involves aneurysms. In particular, abdominal aortic aneurysm (AAA). AAA is a common degenerative vascular disease whose pathogenesis is associated with activation of multiple signaling pathways including Jun NH2-terminal kinases (JNK) and NF-κB. These pathways are chaperoned by HSP90. AAAs occur in ~9% of older men and account for more than 15,000 deaths annually in the United States. Pathological processes of AAA are complex, but mainly characterized by significant degradation of extracellular matrix including elastin and collagen, increased activity of matrix metalloproteinases (MMPs), excessive local inflammation, and neovascularization of the media and adventitia. Currently there is no effective pharmacological therapy available to prevent the development and progression of AAA, and surgical repair of late-stage disease remains the only effective method of reducing aneurysm-related mortality. (Qi, Jia et al. "Heat shock protein 90 inhibition by 17-DMAG attenuates abdominal aortic aneurysm formation in mice." American journal of physiology. Heart and circulatory physiology vol. 308.8 (2015): H841-52. doi:10.1152/ajpheart.00470.2014). Inflammation has been well documented as a hallmark of AAA pathology, which is an early event in clinical aneurysm formation and ANG II-infusion AAA formation in animal models. Recently, it has been increasingly recognized that activation of NF-κB pathway plays an important role in promoting expression of both MMPs and MCP-1, which contributes significantly to the macrophage infiltration during AAA formation. Inhibition of HSP90 in a subject having or at risk of developing aneurysms is a vital therapy to prevent the HSP90-mediated oxidative stress that triggers the MAPk, MMP, and NK-fB pathways otherwise leading to AAA.

Infection and Infectious Disease

Elevated expression of HSP90 has been shown to promote and allow for several different infectious diseases from rhinovirus to HSV-1 and more. Human rhinoviruses (HRV) are positive single-stranded RNA viruses belonging to the family Picornaviridae. HRV infection in humans usually causes common cold and mild illnesses, but is sometimes associated with asthma exacerbation and viral upper respiratory tract infection (Bartlett et al., 2008). HRVs are divided into three distinct species including type A, type B, and type C, with over 100 immunologically non-cross reactive HRV serotypes (Park et al., 2012). Other examples of targeted diseases associated with increased HSP90 expression and activity are influenza, SARS-CoV, HCV, HIV (Li et al., 2004), and herpes viruses (HSV1/2, CMV, VZV) (Sun et al., 2013), as well as against picornaviruses including poliovirus, coxsackievirus, and rhinovirus (Geller et al., 2012). Hsp90 inhibitors are very attractive antiviral agents for infections lacking antiviral therapies and for an urgent response to the outbreak of novel viral diseases. In addition, application of Hsp90 inhibitors to several animal models of infectious diseases was demonstrated to decrease viral replication in case of Poliovirus and HCV infections. (Song J, Shim A, Kim Y, Ahn J, Kwon B, Pham T T, Lee J, Chang S, Ko H. Antiviral and Anti-Inflammatory Activities of Pochonin D, a Heat Shock Protein 90 Inhibitor, against Rhinovirus Infection. Biomolecules & Therapeutics 2018; 26:576-583. https://doi.org/10.4062/biomolther.2017.233).

Accordingly, the administration of a nitroxide antioxidant, such as Tempol, confers beneficial treatment and prevention to infectious diseases through the management and modulation of HSP90 encoding gene expression.

Eye Diseases

The retina is a complex tissue with a high metabolic demand, constantly exposed to stress (Athanasiou et al. 2013). To maintain cell homeostasis and prevent damage, the retina contains high levels of heat shock proteins under normal conditions (Urbak and Vorum 2010). Hsp90 is widely distributed in all retinal layers, from the retinal ganglion cells (RGC) to the inner segment (IS), the tips of the outer segment (OS) and retinal pigment epithelium (RPE) cells (Dean and Tytell 2001). An example of an eye disease that is treatable and preventable by HSP90 inhibition is rentinal pigmentosa (RP). RP is the most common form of inherited photoreceptor degeneration and mutations in the rhodopsin gene are the most common cause of autosomal dominant RP. Studies have shown that in disease models of rhodopsin mutation (R135L) inhibition of Hsp90 was protective. (Aguilà, Mònica, and Michael E Cheetham. "Hsp90 as a Potential Therapeutic Target in Retinal Disease." Advances in experimental medicine and biology vol. 854 (2016): 161-7. doi:10.1007/978-3-319-17121-0_22).

Age-related macular degeneration (AMD) is another example of a disease associated with elevated levels of HSP90 contributing to the development and progress of the disease. AMD is a complex multifactorial disease involving genetic, environmental, metabolic, and functional factors. Functional abnormalities and cell death in the RPE cells contribute to the development of AMD, and are associated with increased oxidative stress (Jarrett and Boulton 2012). Hsp90 is expressed in RPE cells and its expression increases significantly during the progression of AMD (Decanini et al. 2007). Inhibition of HSP90 is effective in blocking both inflammation and neovascularization, two hallmarks of AMD. (Aguilà, 2016).

In eye-related cancers, Hsp90 inhibition is a major target as several aspects of tumor cell viability are reliant on Hsp90 function. Uveal melanoma (UM) is the most common primary intraocular malignancy in adults (Egan et al. 1988) and Hsp90 is emerging as a potentially important target in UM. Focal adhesion kinase (FAK) is a cytoplasmic tyrosine kinase that plays a central role in several cellular processes including mediation of extracellular matrix-integrin signaling, cell migration, invasion and metastasis in several cancers, including UM (Hess et al. 2005). Hsp90 is crucial for the stability and functional conformation of FAK, as inhibition of Hsp90 interferes with its phosphorylation and stimulates its proteasome-mediated degradation (Faingold et al. 2008). Hsp90 inhibition resulted in a reduction of migration and invasion of cancer cells through FAK-mediated pathways (Faingold et al. 2008; Aguilà, 2016).

Administration of a nitroxide antioxidant, such as Tempol, inhibits HSP90 to treat and prevent these eye related diseases. The inhibition of HSP90 reduces inflammation, regulates protein aggregation, regulates neovascularization, and treats the underlying causes of these eye-related diseases.

Methods for Treating Genetic Diseases Associated with Increased HSP90 Activity

Some embodiments disclosed herein provide methods for treating genetic diseases associated with increased HSP90 activity in a human subject in need thereof, comprising (optionally) identifying a human subject having a genetic disease and in need of a decreased expression level of a HSP90 gene; and administering to the human subject an effective amount of a nitroxide antioxidant. In some embodiments, the methods disclosed herein are used to treat a human subject that shows no symptoms of the genetic disease, but is at risk of having the genetic disease. Exemplary risk factors for genetic diseases include, but are not limited to, age, family history, health conditions, medical history, habits, or a combination thereof. In some embodiments, risk factors for genetic disease comprise an increased expression level of HSP90.

In some embodiments, administering to the human subject an effective amount of the nitroxide antioxidant results in a decreased expression level of a gene, for example HSP90. The gene associated with heat shock protein 90 can be HSP90AA1, HSPC1, HSPCA, HSP89, FLJ31884, HSP90N, HSP90AA3P, HSPCAL1, HSP90AB1, HSPC2, HSPCB, HSP90B1, TRA1, GP96, GRP94, TRAP1, HSP75, HSP90L, HSP10, HSP27, Ab-crystallin, HSP40, HSP47 HSP60, HSP70, HSP72, HSP73, HSP75, HSP90, HSP110, HSP110, and HSP105. The treatment of the human subject with the effective amount of the nitroxide antioxidant results in a decreased expression level of the gene. For example, the treatment results in a decreased expression level of HSP90. The decreased expression level of HSP90, decreases the quantity of the encoded protein and improve mitochondrial function activated by increased expression levels. The improved and corrected heat shock protein activity and mitochondrial function reduces, prevents, or eliminates the signs and symptoms of a genetic disease associated with increased HSP90 function, including the curing of the genetic disease.

In some embodiments, the levels of HSP90 in the connective tissue, muscle tissue, nervous tissue, and/or epithelial tissue change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Non-limiting examples of genetic diseases associated with increased HSP90 activity include Osteogenesis imperfecta, Spondyloepiphyseal dysplasia, Spondyloepimetaphyseal dysplasia, Achondrogenesis, hypochondrogenesis, Kniest dysplasia, Stickler syndrome, Ehlers—Danlos syndrome, Familial porencephaly, Hereditary angiopathy with nephropathy, aneurysms and muscle cramps syndrome, Benign familial haematuria, Alport syndrome, Leiomyomatosis, Bethlem myopathy, Ullrich congenital muscular dystrophy, Dystrophic epidermolysis bullosa, Corneal endothelial dystrophies Multiple epiphyseal dysplasia, Autosomal recessive Stickler syndrome, Schmid metaphyseal chondrodysplasia, Marshall syndrome, Otospondylomegaepiphyseal dysplasia Deafness, Junctional epidermolysis bullosa-other Knobloch syndrome Methods for Counteracting Treating a Disease Related to Aging Some embodiments disclosed herein provide methods for counteracting age-related increase in gene expression or treating an age-related disease, comprising (optionally) identifying a human subject over the age of 35 and having an increased expression level of HSP90 or an age-related disease; and administering to the human subject an effective amount of a nitroxide antioxidant. In some embodiments, the methods comprise determining the expression level of HSP90. The identification step and/or the determination step may not be necessary in some instances, such as where an increased expression level of HSP90 can be inferred from the human subject's age, family history, health conditions, medical history, habits, or a combination thereof. In some embodiments, the methods disclosed herein are used to treat a human subject shows no symptoms of an age-related disease, but is at risk of having an age-related disease. Exemplary risk factors for an age-related disease include, but are not limited to, age, family history, health conditions, medical history, habits, or a combination thereof. In some embodiments, risk factors for an age-related disease comprise a increased expression level of HSP90.

In some embodiments, administering to the human subject an effective amount of the nitroxide antioxidant results in a decreased expression level of a gene, for example HSP90. The gene associated with heat shock protein 90 can be HSP90AA1, HSPC1, HSPCA, HSP89, FLJ31884, HSP90N, HSP90AA3P, HSPCAL1, HSP90AB1, HSPC2, HSPCB, HSP90B1, TRA1, GP96, GRP94, TRAP1, HSP75, HSP90L, HSP10, HSP27, Ab-crystallin, HSP40, HSP47 HSP60, HSP70, HSP72, HSP73, HSP75, HSP90, HSP110, HSP110, and H. The treatment of the human subject with the effective amount of the nitroxide antioxidant results in a decreased expression level of the gene. For example, the treatment results in a decreased expression level of HSP90. The decreased expression level of HSP90, corrects mitochondrial function and heat shock protein activity to a healthy level within the cell. The corrected level of heat shock protein activity and mitochondrial function results in a decrease in or disappearance of signs and symptoms of an age-related disease associated with increased HSP90 function, including the curing of the age-related disease.

In some embodiments, the levels of HSP90 in the connective tissue, muscle tissue, nervous tissue, and/or epithelial tissue change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising (optionally) identifying a human subject over the age of 35 and having an age-related disease and having an increased expression level of the HSP90 gene; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with heat shock protein 90 is decreased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising (optionally) identifying a human subject having an increased expression level of a HSP90 gene; and administering to the human subject an effective amount of a nitroxide antioxidant. Some embodiments disclosed herein provide methods for treating a disease associated with increased HSP90 activity in a patient in need thereof, comprising (optionally) identifying a human subject having an increased expression level of HSP90; and administering to the human subject an effective amount of a nitroxide antioxidant. The increased expression level may be age-related, or disease related. In some embodiments, the disease is be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising (optionally) identifying a human subject over the age of 35 in need of a decreased expression level of a HSP90 gene; and administering to the human subject an effective amount of a nitroxide antioxidant. In some embodiments, the methods comprise determining the expression level of HSP90. In some embodiments, the determination step comprises inferring increased expression level of HSP90 based on the human subject's age, family history, health conditions, medical history, habits, or a combination thereof. In some embodiments, the methods disclosed herein may be used to treat a human subject shows no symptoms of a disease associated with increased HSP90 function, but is at risk of having a disease associated with increased HSP90 function. Exemplary risk factors for a disease associated with increased HSP90 function include, but are not limited to, age, family history, health conditions, medical history, habits, or a combination thereof.

In some embodiments, administering to the human subject an effective amount of the nitroxide antioxidant results in a decreased expression level of a gene, for example a gene associated with heat shock protein activity. The gene associated with heat shock protein 90 can be HSP90. The treatment of the human subject with the effective amount of the nitroxide antioxidant results in a decreased expression level of the gene. For example, the treatment decreases the expression levels of HSP90. The decreased expression of the gene counteracts the increase in the expression level of the gene.

Methods for Treating Cancer

Some embodiments disclosed herein provide methods for treating cancer in a human subject in need thereof, comprising (optionally) identifying a human subject having a cancer and in need of a decreased expression level of a HSP90 gene; and administering to the human subject an effective amount of a nitroxide antioxidant. In some embodiments, the methods disclosed herein may be used to treat a human subject that shows no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of HSP90.

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MRI for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MM); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in a decreased expression level of a gene, for example a gene associated with heat shock protein activity. The gene associated with heat shock protein 90 can be HSP90AA1, HSPC1, HSPCA, HSP89, FLJ31884, HSP90N, HSP90AA3P, HSPCAL1, HSP90AB1, HSPC2, HSPCB, HSP90B1, TRA1, GP96, GRP94, TRAP1, HSP75, HSP90L, HSP10, HSP27, Ab-crystallin, HSP40, HSP47 HSP60, HSP70, HSP72, HSP73, HSP75, HSP90, HSP110, HSP110, and H. The treatment of the human subject with the effective amount of the nitroxide antioxidant results in a decreased expression of the gene. For example, the treatment results in a decreased expression level of HSP90. The decreased expression level of the gene can modulate mitochondrial function and heat shock protein activity to a healthy rate and function. The improved mitochondrial function and heat shock protein activity results in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising (optionally) identifying a human subject having an autoimmune disease and in need of a decreased expression level of a HSP90 gene; and administering to the human subject an effective amount of a nitroxide antioxidant. In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a increased expression level of HSP90.

In some embodiments, Autoimmunity is the system of immune responses of an organism against its own healthy cells and tissues. Any disease that results from such an aberrant immune response is termed an "autoimmune disease". Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Autoimmune diseases are very often treated with steroids.

In some embodiments, administering to the human subject an effective amount of the nitroxide antioxidant results in a decreased expression level of a gene, for example a gene associated with heat shock protein activity. The gene associated with heat shock protein 90 can be HSP90AA1, HSPC1, HSPCA, HSP89, FLJ31884, HSP90N, HSP90AA3P, HSPCAL1, HSP90AB1, HSPC2, HSPCB, HSP90B1, TRA1, GP96, GRP94, TRAP1, HSP75, HSP90L, HSP10, HSP27, Ab-crystallin, HSP40, HSP47 HSP60, HSP70, HSP72, HSP73, HSP75, HSP90, HSP110, HSP110, and H. The treatment of the human subject with the effective amount of the nitroxide antioxidant results in a decreased expression level of the gene. For example, the treatment results in a decreased expression level of HSP90. The decreased expression levels of HSP90, improves mitochondrial function and heat shock protein activity resulting in a decrease in or disappearance of signs and symptoms of the autoimmune disease, including the curing of the autoimmune disease. In some embodiments, the decreased expression level of HSP90, improves mitochondrial function. The improved mitochondrial function results in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *Mycobacterium avium* intracellulare, *Mycobacterium tuberculosis*, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Nitroxide Antioxidant

Nitroxide antioxidants describes a group of stable organic molecules, containing the nitroxyl group >N—O. with an unpaired electron. They have a low molecular weight, are non-toxic, do not elicit immunogenic effects on cells and easily diffuse through cell membranes. Their biological activity as antioxidants is related to the regulation of redox state in the cells. Nitroxides can undergo cyclic oxidation or reduction reactions. Their antioxidant activity is related to several mechanisms such as the direct scavenging of free radicals, transition metal ion oxidation. In addition, nitroxides exhibit superoxide dismutase (SOD)-like activity, modulate its catalase-like activity and ferroxidase-like activity, and are the inhibitors of free radical reactions such as lipid peroxidation. Nitroxides have dynamic beneficial impact on all cellular processes from inhibition of oxidative stress and reducing inflammation, while under certain conditions they may also lead to its intensification, for example, in tumor cells. The different beneficial impact on cellular processes provides each cell with necessary support to prevent or reverse diseases and conditions through optimizing cellular activity and associated biological processes in a healthy state and promoting cell death in diseases such as cancer.

Cyclic nitroxides, also known as aminoxyls or nitroxyls, are stable free radicals stabilized by methyl groups at the α position in five-membered pyrrolidine, pyrroline or oxazolidine and six-membered piperidine ring structures. The methyl groups confer stability to the nitroxide radicals by preventing radical-radical dismutation and also limit access to reactive substances, which can quench the radical species. The substituent groups on the ring (denoted by R—) produce a diverse range of compounds that can be directed to specific hydrophilic or hydrophobic regions in the cellular microenvironment. The redox transformations between the oxidation states of nitroxide, hydroxylamine and the oxoammonium cation acts as an efficient redox couple, which can support catalytic processes via reversible electron redox reactions. (Soule, Benjamin P et al. "The chemistry and biology of nitroxide compounds." Free radical biology & medicine vol. 42.11 (2007): 1632-50. doi:10.1016/j.freeradbiomed.2007.02.030).

The mechanism of action exerted by nitroxide antioxidants is very unique. In particular, nitroxide antioxidant function is characterized by a catalytic mechanism of action associated with a single-electron redox cycle. Their reduction results in the generation of hydroxylamine and oxidation in oxoammonium ion; meanwhile both reactions are reversible and repetitive such that the ratio of free radicals suppressed by nitroxide antioxidants is significantly higher than natural antioxidant processes within a cell. Hydroxylamine also exhibits antioxidant properties because it is easily oxidized to nitroxide. As mentioned above, the nitroxides devoid of electrical charge easily diffuse through the cell membranes, thus they can also inactivate the reactive oxygen species formed in the cells and modulate the concentration of intracellular nitric oxide. Their molecular structure and composition make nitroxide antioxidants additionally efficacious in tissues that prevent transport of different molecules, such as neuronal tissue across the blood brain barrier.

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Amin omethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, 2,2,6,6-tetramethyl-4-oxo-1-piperidinyloxy (TEMPONE), 1-Hydroxy-2,2,6,6-tetramethyl-4-oxo-piperidine. HCl (TEMPONE-H), 1,2-dipalmitoyl-sn-glycero-3-phospho(tempo)choline (TEMPO PC), (4-[N,N-dimethyl-N-(2-hydroxyethyl)]ammonium-2,2,6,6-tetramethylpiperidine-1-oxyl (TEMPO Choline), and the like.

The use of other nitroxide compounds is also contemplated. Nitroxide stable radicals demonstrate effective antioxidative activity in various biological systems ranging from molecular, cellular, and laboratory animal level. Nitroxides have been reported to catalyze O2. dismutation through two different catalytic pathways including reductive and oxidative reaction mechanisms. Conversely, kinetics analysis of rapid mixing stopped flow experiments designed to measure the effect of nitroxides on superoxide decay did not reveal any SOD activity, leading to the conclusion that nitroxides act as free radical scavengers.

Studies have shown that unlike other antioxidants, nitroxides are characterized by a catalytic mechanism of action associated with a single-electron redox cycle. Their reduction results in the generation of hydroxylamine and oxidation in oxoammonium ion; meanwhile both reactions are reversible. Hydroxylamine also exhibits antioxidant properties because it is easily oxidized to nitroxide. Nitroxide antioxidants undergo redox cycles. They are easily reduced to hydroxylamines and oxidized to oxoammonium salts.

According to certain embodiments the nitroxide compound can be selected from the following formulas:

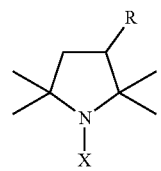

wherein X is selected from O— and OH, and R is selected from COOH, CONH, CN, and CH2NH2;

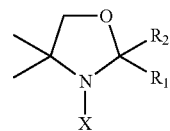

wherein X is selected from O— and OH, and R1 is selected from CH3 and spirocyclohexyl, and R2 is selected from C2H5 and spirocyclohexyl;

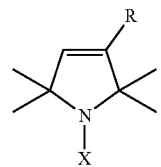

wherein X is selected from O— and OH and R is selected from CONH; and

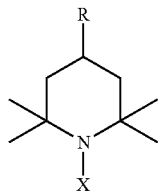

wherein X is selected from O— and OH and R is selected from H, OH, and NH2.

Suitable nitroxide compounds can also be found in Proctor, U.S. Pat. No. 5,352,442, and Mitchell et al., U.S. Pat. No. 5,462,946, both of which are hereby incorporated by reference in their entireties.

In some embodiments, the nitroxide antioxidant has a general formula:

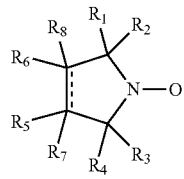

wherein the dashed line denotes a saturated bond or an unsaturated bond, wherein when the dashed line denotes an unsaturated bond, R7 and R8 are absent; R1-R4 are each independently a C1-4-alkyl, or alternatively, R1 and R2, and/or R3 and R4, together form a 3-7-membered alicyclic ring; and R5-R8 are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino.

In some embodiments, the nitroxide antioxidant includes or is associated with (e.g., binds to or is conjugated with) a bioeffector molecule. For example, the bioeffector molecule is a targeting subunit bound to the nitroxide antioxidant, such as a mitochondrial targeting subunit. A targeting subunit can direct activity of the nitroxide antioxidant to a predetermined location within or on the cell. Non-limiting examples of mitochondrial targeting bioeffector molecules includes triphenylphosphine (TPP), gramicidin, and any functional group effectively charged to be attracted to the polarized mitochondria.

In some embodiments, the nitroxide antioxidant is structurally cyclic having a ring structure including a nitroxide molecule incorporated therein. In some embodiments, the nitroxide antioxidant is characterized as the nitroxide molecule functioning as the catalytic center.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 4000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g., lactose, mannitol, glucose, microcrystalline cellulose, starch), combining agents (hydroxypropyl cellulose, polyvinyl pyrrolidone or magnesium metasilicate aluminate), disintegrating agents (e.g., cellulose calcium glycolate), lubricating agents (e.g., magnesium stearate), stabilizing agents, agents to assist dissolution (e.g., glutamic acid or aspartic acid), or the like. The agents may, if desired, be coated with coating agents (e.g., sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g., purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g., glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g., stabilizing agents (e.g., sodium sulfite hydride), isotonic buffers (e.g., sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

Some aspects of the embodiments discussed above are disclosed in further detail in the following examples, which are not in any way intended to limit the scope of the present disclosure.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with Heat Shock Protein Activity To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that HSP90 exhibited statistically significant decrease in expression. This result is shown in Table 1.

TABLE 1

Decreased Expression of HSP90 In Cardiac Tissue After Tempol Administration

| Symbol | Gene title | Fold change |
|---|---|---|
| HSP90 | Heat Shock Protein 90 | −2.4 |

Example 2. Treating Age-Related Increase in Gene Expression

A 70-kilogram human subject over the age of 65 is identified as having, or known to have, or suspected of having an increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 3. Treating a Human Subject with Increased Gene Expression

A 70-kilogram human subject is identified as having, or known to have, or suspected of having an increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 4. Treating a Human Subject with an Age-Related Disease

A 70-kilogram human subject over the age of 65 and having a cardiovascular disease is identified for an increased expression level of HSP90. Or a 70-kilogram human subject over the age of 65 is known to have a cardiovascular disease and/or increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 5. Treating a Human Subject at Risk of Developing Cancer

A 70-kilogram human subject at risk of developing colorectal cancer is identified for increased expression level of HSP90. Or a 70-kilogram human subject is known to be at risk of developing colorectal cancer and/or have increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 6. Treating a Human Subject at Risk of Developing an Autoimmune Disease A 70-kilogram human subject at risk of developing an autoimmune disease (e.g., rheumatoid arthritis) is identified for increased expression level of HSP90. Or a 70-kilogram human subject is known to be at risk of developing an autoimmune disease and/or have increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 7. Treating a Human Subject at Risk of Developing a Condition Due to Aging A 70-kilogram human subject of 45 years old at risk of developing a condition due to aging is identified. Or a 70-kilogram human subject of 45 years old is known to be at risk of developing a condition. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 8. Treating a Human Subject at Risk of Developing a Neruodegenerative Disease A 70-kilogram human subject at risk of developing a neurodegenerative disease (e.g., Parkinson's Disease) is identified for increased expression level of HSP90. Or a 70-kilogram human subject is known to be at risk of developing a neurodegenerative disease and/or have increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

Example 9. Treating a Human Subject Having an Infection

A 70-kilogram human subject having an infection (e.g., a bacterial, fungal, or viral infection) is identified for increased expression level of HSP90. Or a 70-kilogram human subject is known to have an infection and/or have increased expression level of HSP90. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of HSP90, is decreased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of decreasing expression level of one or more genes encoding HSP90, the method comprising:
    administering an effective amount of a nitroxide antioxidant to a subject having or at risk of an increased expression level of one or more genes expressing HSP90, wherein the expression level of the one or more genes encoding HSP90 is decreased.

2. The method of claim 1, wherein the subject has a disease associated with increased expression levels of one or more genes encoding HSP90.

3. The method of claim 1, wherein the subject has a vascular disease.

4. The method of claim 1, wherein decreasing the expression level of the one or more genes treats a disease caused by increased heat shock protein activity.

5. The method of claim 1, wherein the subject has or is at risk of developing cancer.

6. The method of claim 1, wherein the subject has a disease associated with respiratory inflammation.

7. The method of claim 1, wherein the subject has a neurodegenerative disease.

8. The method of claim 1, wherein the decreased expression level of one or more genes encoding a heat shock protein reduces a rate of senescence.

9. The method of claim 1, wherein the subject has atherosclerosis.

10. The method of claim 1, wherein the subject has elevated expression levels of HIF1a, and wherein the administration of the nitroxide antioxidant destabilizes HIF1a.

11. The method of claim 1, wherein the nitroxide antioxidant is 4-hydroxy-2,2,6,6-tetramethylpiperidine-1-oxyl.

12. The method of claim 1, wherein the subject has one or more tumors, and wherein the decreased expression of HSP90 reduces the size of the one or more tumors.

* * * * *